United States Patent
Cerwin et al.

(10) Patent No.: US 8,337,433 B2
(45) Date of Patent: Dec. 25, 2012

(54) TIME-REVERSED MIRRORING ELECTRO-MAGNETIC ACOUSTIC TREATMENT SYSTEM

(76) Inventors: Stephen Anthony Cerwin, Mico, TX (US); David B. Chang, Tustin, CA (US); Jane Emerson, Irvine, CA (US)

(*) Notice: Subject to any disclaimer, the term of this patent is extended or adjusted under 35 U.S.C. 154(b) by 222 days.

(21) Appl. No.: 12/786,232

(22) Filed: May 24, 2010

(65) Prior Publication Data

US 2011/0288450 A1 Nov. 24, 2011

(51) Int. Cl.
*A61H 1/00* (2006.01)
(52) U.S. Cl. .................................................. 601/2
(58) Field of Classification Search .................. 601/2
See application file for complete search history.

(56) References Cited

U.S. PATENT DOCUMENTS

| | | | |
|---|---|---|---|
| 5,428,999 | A | 7/1995 | Fink |
| 5,910,857 | A | 6/1999 | Scott et al. |
| 6,535,625 | B1 | 3/2003 | Chang et al. |
| 6,755,083 | B2 | 6/2004 | Berryman |
| 6,974,415 | B2 | 12/2005 | Cerwin et al. |
| 7,411,445 | B2 | 8/2008 | Kucherov et al. |
| 2002/0051751 | A1 | 5/2002 | Mills |
| 2004/0059265 | A1 | 3/2004 | Candy et al. |
| 2004/0267111 | A1* | 12/2004 | Feinberg ............ 600/411 |
| 2007/0038060 | A1* | 2/2007 | Cerwin et al. ...... 600/407 |
| 2008/0008369 | A1* | 1/2008 | Koptenko et al. .... 382/128 |
| 2008/0045864 | A1 | 2/2008 | Candy et al. |
| 2008/0200803 | A1* | 8/2008 | Kwon et al. ........ 600/430 |
| 2009/0105588 | A1 | 4/2009 | Emelianov et al. |

FOREIGN PATENT DOCUMENTS

WO 2009/091597 7/2009

OTHER PUBLICATIONS

Fink, Mathias, "Time Reversal of Ultrasonic Fields—Part I: Basic Principles", IEEE Transactions of Ultrasonics, Ferroelectrics, and Frequency Control, vol. 39, No. 5, Sep. 1992.
Fink, Mathias, "Time Reversal of Ultrasonic Fields—Part I: Experimental Results", IEEE Transactions of Ultrasonics, Ferroelectrics, and Frequency Control, vol. 39, No. 5, Sep. 1992.
Gencer, Nevzat G., Tek, M.Nejat, "Imaging Tissue Conductivity via Contactless Mesaurements: A Feasibility Study", Elektrik, vol. 6, No. 3, 1998.

* cited by examiner

*Primary Examiner* — Tse Chen
*Assistant Examiner* — Hien Nguyen
(74) *Attorney, Agent, or Firm* — Fish & Associates, PC

(57) ABSTRACT

A time-reversal mirroring electromagnetic acoustic treatment system is disclosed where electro-magnetic signals are directed to a region of interest in or on a patient. The EM signals induce an internally sourced acoustic signal due to variations in conductivity of the target tissue. Acoustic data representative of the induced acoustic signal are collected and analyzed to develop a model of a measured conductivity topology representing the conductivity topology of the target tissue. Measured parameters associated with the measured conductivity topology and derived from the acoustic data can be used to generate a time-reversed mirror acoustic treatment signal that can be used to apply a therapeutic treatment to a target tissue within the region of interest.

15 Claims, 5 Drawing Sheets

TIME-REVERSED MIRRORING ELECTRO-MAGNETIC ACOUSTIC TREATMENT SYSTEM

FIELD OF THE INVENTION

The field of the invention is acoustic medical technologies.

BACKGROUND

Electro-Magnetic Acoustic Imaging (EMAI) technologies have developed significantly over the last several decades; in a large part to the Applicants' own seminal works. For example, EMAI technologies are described in great detail in co-owned U.S. Pat. No. 6,535,625 to Chang et al. titled "Magneto-Acoustic Imagining" filed on Sep. 24, 1999 and co-owned U.S. Pat. No. 6,974,415 to Cerwin et al. titled "Electromagnetic-Acoustic Imagining" filed on May 22, 2003.

It was appreciated early on that one could use Time-Reversed Mirroring (TRM) of ultrasonic signals to treat target tissues. For example, the papers titled "Time Reversal of Ultrasonic Fields—Part I: Basic Principles" and "Time Reversal of Ultrasonic Fields—Part II: Experimental Results" by Fink et al., published in September 1992, describe in great detail time reversing ultrasonic acoustic signals. Further effort toward developing TRM ultrasound technologies is described in U.S. Pat. No. 5,428,999 to Fink titled "Method and Apparatus for Acoustic Examination Using Time Reversal" filed on Sep. 24, 1993, and U.S. Pat. No. 6,755,083 to Berryman titled "Method for Distinguishing Multiple Targets Using Time-Reversal Acoustics" filed Apr. 22, 2002.

The Applicants also provided pioneering insight into combining the two technologies where electro-magnetically induced acoustic ultrasounds could be time-reversed and mirrored back toward an originating internal target tissue as described in U.S. patent application publication U.S. 2007/0038060 to Cerwin et al. titled "Identifying and Treating Bodily Tissues Using Electromagnetically Induced, Time-Reversed, Acoustic Signals" filed on Jun. 9, 2006. At the time, the Applicants focused on applying an amplified TRM ultrasound signal back toward a detected conductivity gradient, possibly to ablate a target tissue.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

The Applicants have come to further appreciate that a wealth of information is available regarding a subject area of interest that can be brought to bear when constructing a TRM ultrasound signal to target a specific tissue. Previously, induced ultrasound signals were filtered to enhance reception of only signals having a frequency twice the frequency of an input RF signal. Additionally, the received ultrasound signals were only mirrored back toward a conductivity gradient. Applicants have now appreciated received acoustic data of an induced acoustic signal represents a measurement of a conductive topology, as opposed to just an indicator that a conductivity gradient is present. The acoustic data reflects properties of a full conductivity topology and by extension properties of the tissues within the subject area under consideration. One can collect and use the acoustic data to derive parameters associated with the conductivity topology to deduce or derive various properties of the subject tissue area. The measured parameters can then be used to tailor a TRM acoustic treatment signal to apply therapy to a target tissue within the subject area. One should appreciate that conductivity topologies can be combined with other topologies (e.g., mechanical, acoustic, density, etc.) to create a hybrid topology that can be brought to bear for clinically useful results (e.g., diagnosis, treatment, etc.)

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Thus, there is still a need for time-reversed mirroring of electro-magnetically induced acoustic signals.

SUMMARY OF THE INVENTION

The inventive subject matter provides apparatus, systems and methods in which one can utilize a system for identifying a target tissue for therapy based on detected properties of a conductivity topology of a subject tissue area. One aspect of the inventive subject includes a Time-Reversed Mirroring (TRM) Electro-Magnetic Acoustic (EMA) treatment system. Contemplated systems comprise an Electro-Magnetic (EM) signal source configured to emit EM radiation, preferably in the radio frequency range, toward a subject area having one or more tissues. Tissues in a subject area typically have different mechanical, chemical, or electrical proprieties. Due to variations in such properties, the tissues can exhibit a conductivity gradient that reacts in response to being bathed by the EM radiation. The reaction can be generating induced acoustic signals, typically UltraSound (US). TRM EMA treatment systems can also include an array of acoustics transducers configured to receive the induced acoustic signals generated from within the subject area. The transducer array can provide to a TRM controller acoustic data representative of the received induced acoustic signal. Preferably the TRM controller collects and analyzes the acoustic data from the transducer array. Through analysis of the acoustic data, the TRM controller can derive a measured conductivity topology of at least a portion of the subject area based on the properties of the acoustic data (e.g., frequency, signal strength, noise level, signal-to-noise ratio, phase, time of flight, etc.). The TRM controller can also generate a set of instructions for acoustic emitters. The instructions represent control signals to the array of acoustic emitters, preferably the array of transducers, to emit a time reversed acoustic signal back toward the subject area, preferably directed to a target tissue selected based on the measured parameters as determined from the measured conductivity topology.

One should appreciate that the time reversed acoustic signals can be controlled through the TRM controller. In some embodiments, the time reversed acoustic signal represents a time reversed mirrored version of the received electromagnetically induced acoustic signal. The time reversed acoustic signal can also be constructed based one or more properties of the measured conductivity topology as derived from the received acoustic data. Constructing the time reversed acoustic signal provides for tailoring a specific acoustic treatment or targeting specific tissues exhibiting interesting properties. The properties of the measured conductivity topology can include geometry, signal-to-noise ratio, conductivity, location, or other parameters measured from the acoustic data. It is also contemplated that the time reversed acoustic signal can be constructed based on other information as well, possibly including EM reflections, mechanical properties, input from a healthcare provider, programmatic data, or other information.

Furthermore, the time reversed acoustic signal can be constructed so that it targets a specific tissue within the subject area based on the target tissue's contribution to the conductivity topology or even if it lacks a substantial contribution to the measured topology. As an example, the contemplated system can construct the time reversed acoustic signal, possibly a conductivity weighted treatment signal, so that it has sufficient gain to ablate at least a portion of a target tissue.

Various objects, features, aspects and advantages of the inventive subject matter will become more apparent from the following detailed description of preferred embodiments, along with the accompanying drawing figures in which like numerals represent like components.

DETAILED DESCRIPTION

Throughout the following discussion, numerous references will be made regarding sources, controllers, apparatus, systems, or other forms of computing devices. It should be appreciated that the use of such terms is deemed to represent one or more computing devices having at least one processor configured to execute software instructions stored on a computer readable medium. For example, a controller can include one or more computers operating as a management device controlling other devices in a manner to fulfill described roles, responsibilities, or functions. One should appreciate that the disclosed techniques provide many advantageous technical effects including generation and application of therapeutic acoustic signals to be applied to target tissues.

Figure 1:
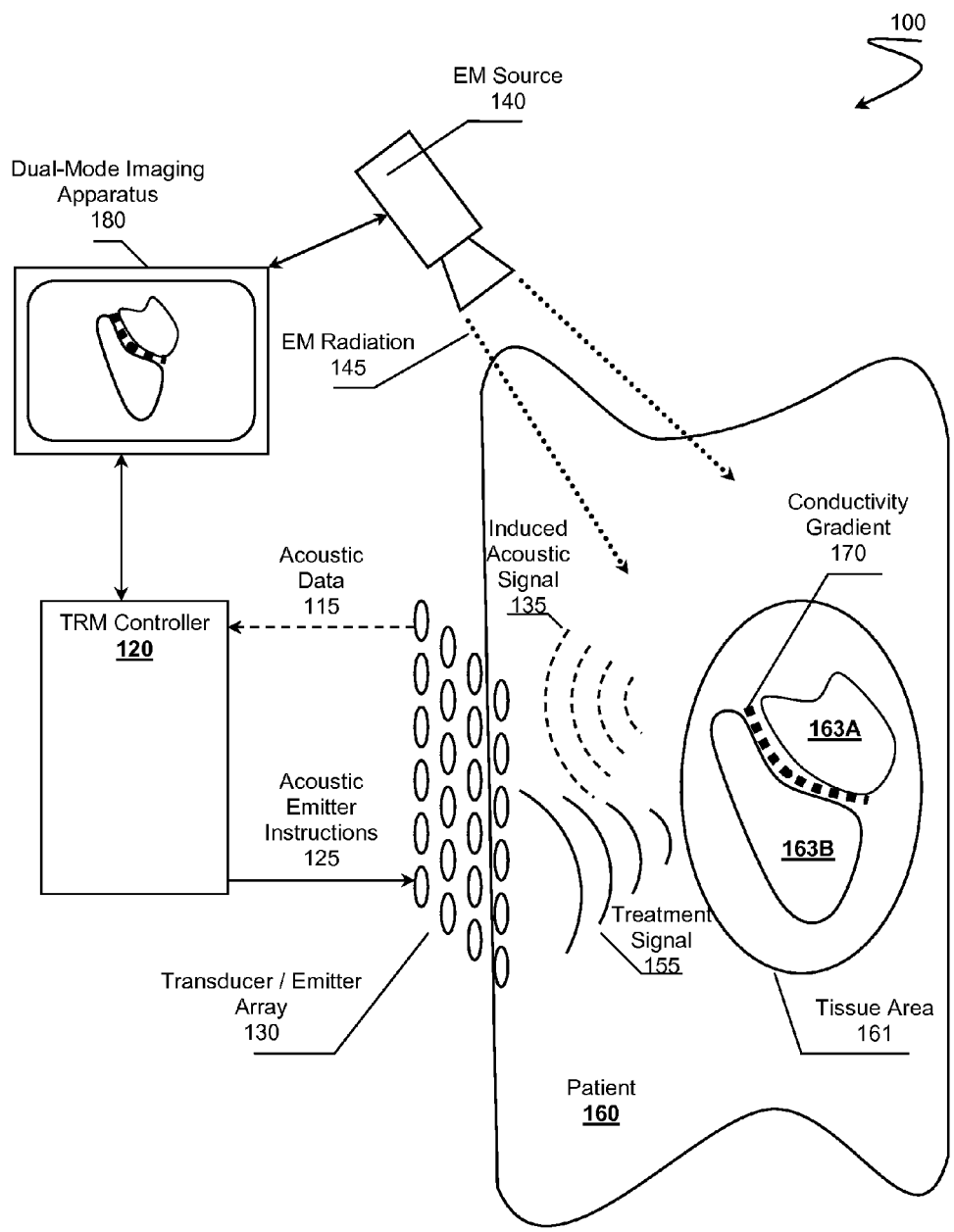
FIG. 1 is an overview of a time-reversal mirroring electromagnetic acoustic treatment system.

In FIG. 1, Time-Reversed Mirroring (TRM) Electro-Magnetic Acoustic (EMA) treatment system 100 can comprise several components. In some embodiments, at least some of the components can be combined to form single integral devices, even a portable device. In other embodiments the components can be physically distributed where the components exchange data over a communications network, wired or wireless. In more preferred embodiments, the components communicate over a wired network to reduce possible EM interference. It is also contemplated the components could communicate over an optic fiber network to reduce metal components. Such an approach is considered an advantage when the components are used within conjunction of a strong magnetic field generator.

A brief theoretical overview will aid the reader in understanding the disclosed concepts. System 100 can comprise EM source 140 that emits RF EM radiation signal 145 toward tissue subject area 161 within patient 160. In the example shown, tissues 163A or 163B within subject area 161 can comprise one or more of conductivity gradient 170, typically located at a boundary between tissues. As EM radiation signal 145 impinges on gradient 170, radiation signal 145 induces gradient 170 to generate an acoustic signal 135 (e.g., ultrasound). Induced acoustic signal 135 can be detected, time-reversed, and amplified to generated treatment signal 155 that is directed back toward gradient 170. The Applicant's own work provides a detailed discussion regarding induced acoustic signals and using a TRM treatment signal as discussed in co-owned U.S. Pat. No. 6,535,625 to Chang et al. titled "Magneto-Acoustic Imagining" filed on Sep. 24, 1999 and co-owned U.S. Pat. No. 6,974,415 to Cerwin et al. titled "Electromagnetic-Acoustic Imagining" filed on May 22, 2003, and in U.S. patent application publication U.S. 2007/0038060 to Cerwin et al. titled "Identifying and Treating Bodily Tissues Using Electromagnetically Induced, Time-Reversed, Acoustic Signals" filed on Jun. 9, 2006. The Applicants' previous approaches failed to appreciate that a TRM acoustic treatment signal 155 can be constructed or otherwise generated to have desired properties based on the full conductivity topology of the region rather than merely mirroring an induced acoustic signal back toward conductivity gradient 170. The Applicants' previous approaches also failed to appreciate interactively monitoring various measured parameters associated with a conductivity topology or adjusting therapeutic treatment signals accordingly (e.g., real-time ablation, focus, shape, etc.).

EM source 140 is configured to emit Radio Frequency (RF) signals toward subject area 161. Preferred RF signals comprise a frequency in the range from 1 MHz to 500 MHz, more preferably from 1.0 MHz to 400 MHz, and yet more preferably from 1 MHz to 20 MHz. EM source 140 can also take on many different forms including a Helmholtz coil, a magnetic resonance imaging system, or other apparatus capable of generating the desirable RF signals. Furthermore, EM source 140 can be configured to emit two or more distinct signals (e.g., RF signals having distinct peaks) or a spectrum of signals, which can be used for diagnostic or therapeutic purposes as discussed below. Transmitted signals are discussed further with respect to FIGS. 4A and 4B.

Input signal 145 can be generated according to any desired function. In some embodiments, signal 145 could include a single, persistent dominate frequency peak. In other embodiments, signal 145 could include multiple, distinct frequency peaks (See FIGS. 4A and 4B). In yet other embodiments signal 145 can be chirped (e.g., has a specified rate of frequency change, up or down). Regardless of the form of signal 145, the inventive subject matter is considered to include identification, diagnosis, or treatment of target tissues based on the various input properties of signal 145 (e.g., frequency, chirp, phase, amplitude, spectrum, etc.)

System 100 also preferably includes transducer array 130 comprising a plurality of individual transducers adapted to collect acoustic signals 135 originating from patient 160. Acceptable transducers can be based on piezoelectric crystals adapted to convert acoustic signals 135 into acoustic data 115. Acoustic data 115 can include electrical signals representative of induced acoustic signal 135. The transducers of array 130 can also function as acoustic emitters that can direct acoustic signals back toward patient 160 as governed by acoustic emitter instructions 125. The emitted acoustic signals can take the form of treatment signal 155 generated to target a target tissue, tissues 163A or 163B for example.

Array 130 can be arranged according to various geometries to best suit a target patient or therapy. Contemplated geometries include one or more linear arrays, annular arrays, rectangular arrays, combinations arrays, flexible sheet of arrays, three dimensional arrays, or other configurations. A preferred array comprises an area covering capability to ensure suitable acquisition of acoustic data 115 originating from patient 160.

Additionally, preferred arrays provide for directing treatment signal 155 toward a target tissue.

Although array 130 is illustrated as both a receiver and emitter, it is also contemplated that two or more arrays could be used to serve various functional roles. For example, a first array 130 could be placed on an upper surface of patient 160 to collect induce acoustic signal 135 while a second array could be place under patient 160 to emit treatment signal 155. In embodiments having multiple arrays 130, each array can be individually configured to receive induced acoustic signal 135, to emit treatment signals 155, to provide constructive or destructive interface with other arrays, to shape treatment signal 155, or to operate as desired under control of TRM controller 120. In some embodiments, one array 130 could emit a TRM signal while another array emits a constructed treatment signal lacking a TRM component of induced acoustic signal 135.

Array 130 can be placed directly on patient 160 or placed adjacent to an intermediary material that is in direct physical contact with patient 160. For example, patient 160 could be covered with an acoustic gel through which array 130 transmits or receives acoustic signals.

Preferred embodiments of system 100 also include TRM controller 120 capable of receiving acoustic data 115, analyzing acoustic data 115, and generating acoustic emitter instructions 125. Preferably TRM controller 120 generates acoustic emitter instructions 125 based on properties of subject area 161 as determined from a measured conductivity topology as discussed below. Acoustic emitter instructions 125 represent control signals sent to array 130 that instruct array 130 to emit treatment signal 155. One should appreciate that treatment signal 155 comprises an aggregation of acoustic signals individually emitted by each transducer of array 130. Treatment signal 155 can be constructed based on calculations performed by TRM controller 120, or could minimally be a TRM version of induced acoustic signal 135.

TRM controller 120 can also be coupled to imaging apparatus 180, which visually displays image data related to subject area 161 as derived from acoustic data 115. In the example shown, imaging apparatus 180 receives input from both TRM controller 120 and EM source 140 to display an image. For example, where EM source 140 includes an MRI apparatus, output from the MRI apparatus can be overlaid with the TRM controller's acoustic imaging data to generate a composite image for at least a portion of subject area 161. Imaging data from TRM controller 120 can include digital models constructed from acoustic data 115 where the digital models can provide details about tissue subject area 161, possibly including tissues 163A or 163B.

Figure 2:
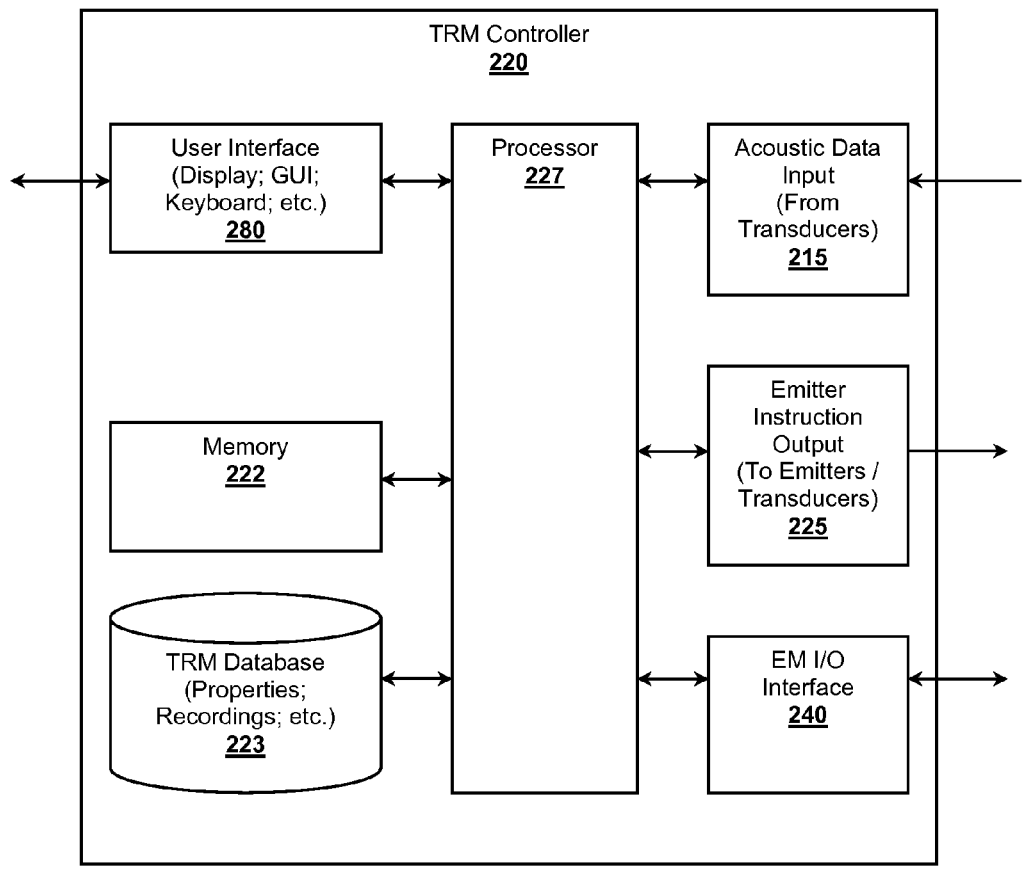
FIG. 2 is a schematic of a possible time-reversal mirroring controller.

FIG. 2 provides a schematic overview of a possible TRM controller 220. In a preferred embodiment, controller 220 comprises a computing device having processor 227 capable of executing one or more software instructions stored in memory 222. In some embodiments, TRM controller 220 can be a desktop computer while in other embodiments controller 220 can be a handled or portable device. Regardless of the physical form of controller 220, controller 220 operates to receive acoustic data from a transducer array, analyze the acoustic data, or generate instructions for the transducer array to emit a treatment signal.

Memory 222 can include any suitable computer readable media including flash, RAM, SRAM, DRAM, hard disk drive, solid state disks, optical media, magnetic media, or other types of memory.

Controller 220 can also include TRM database 223, possibly implemented within a portion of memory 222, where additional information or data can be stored. In some embodiments, TRM database 223 stores information relating to a treatment including patient data, known types of tissues and their properties, treatment parameters, therapy regimes, programmed therapies, or other type information that can be used to construct an acoustic treatment signal. It is also contemplated that TRM database 223 can be used to record treatment sessions, image data derived from inbound acoustic data, transducer array data, management information relating to each transducer, or any other additional information.

Acoustic data input 215 represents an I/O interface to a transducer array, though which controller 220 receives acoustic data collected by the transducer array. Data input 215 could comprise a wired or wireless interface as desired, while a physical wired interface would be more preferable. In some embodiments, data input 215 could comprise a network connection to a remote array. Contemplated interfaces that could be utilized for data input 215 include analog interfaces, digital interface, serial interfaces, Ethernet interfaces, or other types of interfaces for receiving data.

Collected acoustic data can be analyzed according to any desired algorithm. Preferably, the acoustic data is analyzed to derive a conductivity topology a subject area, where the properties of the topology can be used to generate a treatment signal. Furthermore, information stored within TRM database 223 can also be used in conjunction with the collected acoustic data to determine an appropriate treatment signal. For example, acoustic data could be collected from a subject area having a tumor. Controller 220 uses the acoustic data to develop a three dimensional model of the tumor and surrounding areas based on the measured conductivity topology. Controller 220 can consult TRM database 223 to determine a type of tissue, preferably based on stored known acoustic, conductivity, or other characteristics of tissues. The controller can then modify a treatment signal appropriately to target the specific tissue.

Controller 220 can use information from TRM database 223 to provide additional information to a technician. For example, controller 220 can annotate regions of interest on a display, highlight specific area, provide auditory indicators, or other information to help guide a technician operating controller 220.

Controller 220 can also include user interface 280 through which a technician or other user can supply input to or receive output from controller 220. Controller 220 could use interface 280 to provide image data over interface 280. Interface 280 could also allow a technician guide a specific treatment via keyboard, pointer devices, or other inputs. The user input can also be used to modify a treatment signal, possibly through selecting a treatment area, increasing or decreasing amplitude, exposure time, or other treatment parameters. Furthermore, controller 220 can also include I/O interface 240 configured to exchange data with an EM source. Such an embodiment provides for cooperation between devices when gathering data regarding a target tissue.

Controller 220 can generate an acoustic treatment signal based on the information derived from the collected acoustic data, in TRM database 223, from user input gathered through interface 280, imaging information, or other available information. Preferably the acoustic treatment signal can be constructed as a time-reversed mirrored (TRM) signal, where controller 220 instructs the emitter array to generate the TRM treatment signal and to target a target tissue.

Although TRM controller 220, thus far, has been presented in view of a fairly complex computing device capable of constructing a desired TRM treatment signal, one should appreciate that TRM controller 220 can also be passive controller. As passive controller can optionally lack the computational complexity of TRM controller 220, while still operating to control a transducer array, preferably through dedicated (e.g., non-field programmable) hardware. In such an embodiment, the passive controller simply collects acoustic data from the transducer array, and then directly instructs the array, or other emitters, to generate a time reversed mirrored signal, possibly with increased gain for treatment purposes. It should be appreciated that the collected acoustic data or collected induced acoustic signal represents the conductivity topology of the tissue subject area as opposed to a mere conductivity gradient.

It is also contemplated that transducer array can function as a passive controller where each array element merely provides a TRM signal in response to a portion of the induced acoustic signal incident on each element. A preferred passive controller, even in the form of a transducer array, is configured to provide a TRM treatment signal back toward the tissue subject area based on the subject area's conductivity topology. For example, a technician could manually adjust the parameters of the in real-time array as necessary for a desired treatment, even when the passive controller lacks processor 227, database 223, or even memory 222. As the technician observers the conductivity topology via output from the passive controller, the technician can instruct the array to alter the parameters of the returning TRM signal (e.g., gain, focus, phase, chirp, etc.).

As briefly discussed above, one should note that the treatment signal can be a pure time reversed mirrored signal of a received induced acoustic signal, possibly where the gain of the TRM signal is increased to apply a specific treatment to a target tissue. In such an embodiment, the time reversed treatment signal represents a TRM acoustic signal of the original induced acoustic signal. In more preferred embodiments, the time reversed treatment signal represents a constructed or calculated treatment signal where the calculated treatment signal is generated as a function of a measured conductivity topology of a subject tissue area. Contemplated TRM acoustic treatment signals could include TRM components from the original induced acoustic signal or even lack such a component. One should appreciate that controller 220 can construct, shape, focus, or otherwise generate an acoustic treatment signal, which can be applied as an acoustic therapy to a target tissue.

Figure 3A:
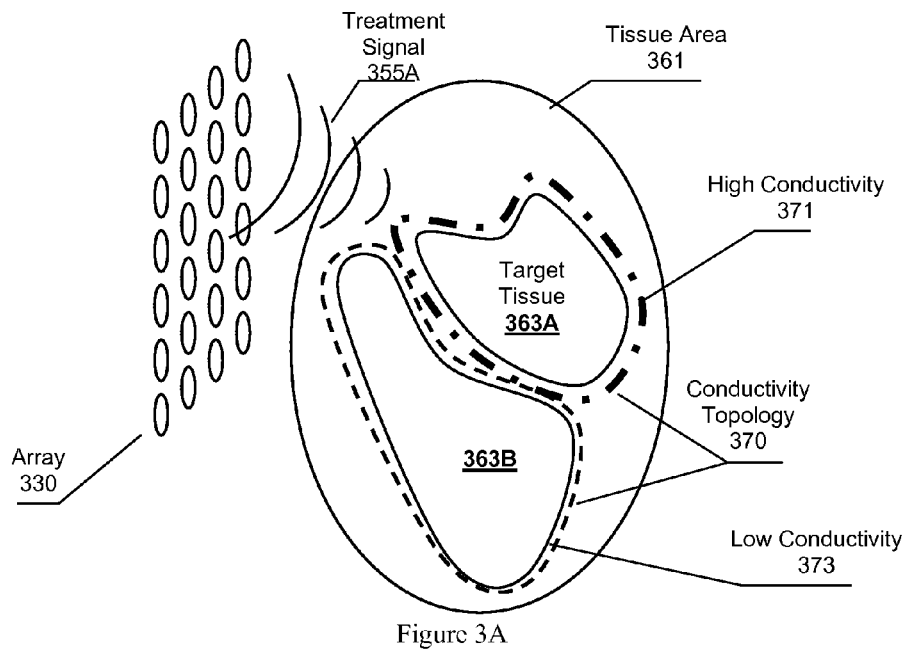
FIG. 3A illustrates targeting a tissue based on a measured conductivity topology of a target tissue.

FIG. 3A provides a more detailed example of how an acoustic treatment signal 355A targets one or more target tissues 363A or 363B based on a measured conductivity topology 370. As discussed previously, RF EM radiation bathes tissue subject area 361, which induces conductivity topology 370 to generate internally sourced acoustic signals (e.g., ultrasound). Previous efforts merely generated an amplified TRM signal that is mirrored back toward a source conductivity gradient. The disclosed approach fully recognizes the acoustic data received from a subject area 361 represents a measure of a full conductivity topology 370, which in turn reflects properties of subject area 361 and its internal tissues 363A or 363B. The measured parameters associated with conductivity topology can then be leveraged for generating treatment signal 355A. In the example shown, conductivity topology 370 comprises a topology associated with two tissues 363A and 363B for illustrative purposes. Naturally, the number and complexity of tissues within a subject tissue area can vary substantially while still falling with in the scope of the inventive subject matter.

A measured conductivity topology represents a model of the conductive structure associated with subject area 361. One should appreciate that measured conductivity topology can be substantially different than other known methods of modeling internal tissues. For example, conventional ultrasound imaging essentially models internal tissues based on differences in the physical density of the tissues. The present inventive subject matter models tissues based on their electrical parameters as derived from acoustic data. The two different models are quite distinct.

Conductivity topology 370 can be defined by a TRM controller according to many different measured parameters derivable from received acoustic data. A measured conductivity topology comprises information relating to the geometric parameters of the conductivity topology 370, including a three dimensional structure. Geometric parameters can include location, size, dimensions, orientation, or other parameters relating to the geometry of topology 370. The geometric parameters of topology 370 can be measured from the collected acoustic data using suitable techniques including those employed for imaging from pulse echo. Imaging based on pulse echo is described more fully in "Fundamentals of Digital Ultrasound Imaging" by C. F. Schuller et al. (IEEE Trans. On Sonics and Ultrasonics, SU-31, 195-217 (1985)), and in "Medical Ultrasound Imaging" by Stephen Hughes (Physics Education, Volume 36, No. 6, 468-475 (2001)). Interestingly, the paper titled "Imaging Tissue Conductivity via Contactless Measurements: A Feasibility Study", by Gencer et al., published in Electrik, Vol. 6, No. 3, 1998, discusses measuring a tissue's conductivity by detecting induced currents, but fails to recognize the measurement of conductivity can be achieved via collection of induced acoustic signal data.

Another contemplated type of parameter by which conductivity topology 370 can be measured includes acoustically measured conductivity parameters. Conductivity parameters represent an actual measure of conductivity from the tissues via analysis of the collected acoustic data. Conductivity can be measured based on the acoustic signal strength resulting from conductivity of the tissue. Some regions of topology 370 can have a high acoustic signal strength representing high conductivity while low conductivity regions will have low acoustic signal strength.

Deriving a measured conductivity from the acoustic data can comprise incorporation of additional data beyond the collected acoustic data. Example additional data that can be used to measure the conductivity can include parameters relating to the transmitted RF radiation (e.g., frequency, spectrum shape, phase, time of flight, direction etc.), characterization data of similar tissues having known conductivity properties, or other data accessible for analysis.

Measured conductivity parameters represent just one class of a broader class of electro-magnetic properties. Electro-magnetic properties of tissues within a tissue subject area are considered to include conductance, resistance or impedance, inductance, capacitance, permittivity, electric susceptibility, dielectric dispersion, dielectric relaxation, or other measurable electro-magnetic parameters that can be derived from the collected acoustic data.

Measured electro-magnetic properties of tissues, including a conductivity gradient, are consider to dependent on one or more properties of an input EM signal. Example input EM signal properties can that can be folded into measuring the electro-magnetic properties of the tissues, or other type of measured parameters, including input frequency, spectrum, phase, amplitude, chirp, or other input properties.

Another type of tissue property that can be measured from a conductivity topology can include mechanical properties. Example mechanical properties can include density, elasticity, Young's modulus, bulk modulus, shear modulus, bending strength, hardness/softness, or other physical properties of tissues.

Yet another type of measurable parameters that can be associated with a measured conductivity topology can include dynamic parameters. Thus far, the above referenced measured parameters have been mainly presented as if they have single static values with respect to time or distance. It should be appreciated that many of the measured parameters can change dynamically with respect to time or geometry. Example dynamic parameters that change in time can include a rate of change, a flow, Doppler shifts, or other temporal based parameters. Example dynamic parameters that change with location or distance include density variations, volume fluctuations, or other changes in values associated with variation in geometry. One should note that a tissue's various electro-magnetic parameters could vary over a volume within the tissue subject area 361. The measurement of such variations from acoustic data is considered to fall within the scope of the inventive subject matter.

The reader should bear in mind a TRM controller providing instructions to array 330 can adjust treatment signal 355A in real-time. As dynamic parameters change in time or geometry, likely due to treatment or movement, the TRM controller can change the treatment signal accordingly. For example, a surface geometry of target tissue 363A or 363B could change, causing measured parameters of their corresponding conductivity topologies to change. Such changes can be used a triggers to adjust a treatment accordingly. Furthermore, a technician can interactively monitor the effects of a treatment via observing changes in the measured parameters. Treatment signal could be adjusted automatically according to a protocol, according to instructions from the technician, or other input.

Still another type of measured parameter includes signal parameters associated with the induced acoustic signal as represented by collected acoustic data. In some embodiments, the signal parameters can be associated with the raw data collected by or derived from transducer array 330, or even each individual transducer of array 330. Signal parameters can include frequency, frequency spectrum, time-of-flight, phase, noise level, signal level, Fourier components, or other measured values derived from the signal of the collected acoustic data.

Of particular note, acoustic data representing induced acoustic signals can include a signal parameter comprising a signal-to-noise ratio (S/N). As acoustic data is collected, the S/N can be calculated for various portions of the measured conductivity topology. In some embodiments, tissues or their properties are characterized by expected S/N as a function of input frequency or spectra. Measured S/N can be compared to expected S/N to properly construct treatment signal 355A. For example, the comparison can be used to identify tissues, selected tissues for treatment, shape treatment signal 355A, focus treatment signal 355A, or other purposes. Additionally, treatment signal 355A could be formed from acoustic data components of the induced acoustic signal that have an S/N greater than a threshold, less than a threshold, or even within an bounded region of S/N values.

Although only a few types of measured parameters of a measured conductivity topology are discussed, all possible measured parameters are contemplated. Furthermore, the measured parameters contribute to building the measured conductivity topology, even where the measured topology includes a three dimensional model of the properties of tissue subject area 361 as derived at least partially from the acoustic data.

As discussed previously, measured parameters of conductivity topology 370 can be considered functions of the properties of an input EM signal. For example, a conductive portion of a tissue might be responsive to varying frequencies because of the tissues electrical properties. At a low frequency, the tissue might not contribute significantly to conductivity topology 370. While the tissue might have a significant contribution at a high frequency. One should also appreciate that tissue properties affect one another; a high conductivity tissue might contribute poorly to a measured conductivity topology if it has a high density. Some measured parameters vary with frequency, even if the frequency variation is within a few MHz of an input signal. Contemplated input EM signal properties that can contribute to the measured parameters include frequency, spectrum, sweep, chirp, phase, or even EM source location.

The above discussed measured parameters contribute to various degrees to the measured conductivity topology of topology 370. In some cases, the contribution of a measured parameter can be significant. For example, a prepared boundary of a tumor, an encapsulated tumor for example, might have a significant conductivity gradient, which would provide a strong induced acoustic signal. Neighboring or surrounding tissues might have a reduced or a low contribution to the measure conductivity topology by having a low conductivity gradient, yielding a low induced acoustic signal. In either case of (a) a measured parameter having a significant contribution or (b) lacking a significant contribute to a measured topology; information derived from the collected acoustic data can be applied toward generating an acoustic treatment signal.

Measured conductivity topologies as discussed above provide a great deal of insight into properties of tissues within tissue subject area 361. One should also appreciate that topological information can be available beyond a measured conductivity topology. Other topologies can include physical topologies, acoustic topologies, or other types of measured topologies that can be derived from other sources (e.g., CT scans, MRI scans, Ultrasounds, etc.). One or more other topologies can be combined with the measured conductivity topology to form a hybrid topology. The values of measured parameters can also depend on information gain from other measured topologies, which can in turn be used to adjust treatment signal 355A.

Treatment signal 355A can be constructed as a function of the measured conductivity topology (e.g., the various measured parameters). In the example shown, treatment signal 355A is generated by transducer array 330 as instructed by a TRM controller. The TRM controller generates instructions so treatment signal 355A would include a TRM component representative of an induced acoustic signal as discussed above. In more preferred embodiments, treatment signal 355A is further constructed as a function of one or more of the measured parameters associated with the measured conductivity topology.

Treatment signal 355A can be constructed by instructing array 330 to create an acoustic signal having various desired acoustic signal properties. Preferably treatment signal 355A has a TRM component as discussed above. In the example shown in FIG. 3A, treatment signal 355A is directed to target tissue 363A, which is considered to have a high conductivity 371 and a significant contribution to the measured conductivity topology as represented by the heavy dashed line associated with the conductivity topology 370. As illustrated, treatment signal 355A is contemplated to include a TRM component of an induced acoustic signal originating from topology 370 (e.g., tissue 363A). In addition, it is specifically contemplated that treatment signal 355A comprises a timereserved acoustic signal having increased gain over that of the induced acoustic signal, where the high gain TRM acoustic treatment signal 355A can be used for therapeutic purposes as discussed further below. In yet more preferred embodiments, treatment signal 355A can also have other constructed properties. For example, treatment signal 355A can be generated to target specific portions of tissues 363A, or can be pulsed or altered with time as desired for a therapy regime.

Of particular note, treatment signal 355A can be constructed to have significant therapeutic value by modifying its properties. By increasing the gain of treatment signal 355A relative to an EM induced acoustic signal, treatment signal 355A can supply a significant amount of sonic energy to target tissue 363A to heat the tissue. In some embodiments, treatment signal 355A has sufficient gain to apply a hyperthermia treatment to target tissue 363A. In addition, the gain could be increased to ablate (e.g., vaporize) target tissue 363A. Such an approach is advantageous for treating tumors or cancerous tissues. The applied hyperthermia treatment could be continuously applied, or applied over multiple treatment sessions separated by minutes, hours, days, weeks, or other time period to allow the patient to recover or heal between treatments.

Given that the disclosed system provides a volumetric approach to measuring conductivity topology, the system preferably comprises sufficient resolution to target a volume within an error ellipsoid having a maximum dimension of no more than 5 mm, more preferably no more than 1 mm, and yet more preferably no more than 0.3 mm. These resolutions can be achieved through higher input frequencies of RF radiation, through increasing resolution of array 330, or positioning transducers. Resolution of array 330 can be increased by increasing transducer density of the array. It is also contemplated that the more detailed resolutions (e.g., less than 0.3 mm) could be achieved through the use of phonon lasers, possibly TRM-based phonon lasers. For example, the phonon laser described in U.S. Pat. No. 7,411,445 to Kurcherov et al. titled "Phonon Laser", filed Apr. 27, 2006, could be adapted for use with the disclosed techniques to achieve resolutions less than 100 μm.

One should appreciate the disclosed techniques can be applied in conjunction with other forms of therapy. It is also contemplated that use of the disclosed techniques is expected to reduce the need for more invasive forms of treatment, surgery, radiation, or chemotherapy for example. It is also contemplated the disclosed techniques could be used to internally tag target tissue 363A by sonically branding tissue 363A so a surgeon can easily identify a target tissue during surgery.

FIG. 3A illustrates using treatment signal 355A to target a high conductivity tissue, tissue 363A. An astute reader will appreciate that conductivity topology 370 will likely have contours, shapes, or other variations in measured parametric values. These can also be used to construct an acoustic treatment signal.

Figure 3B:
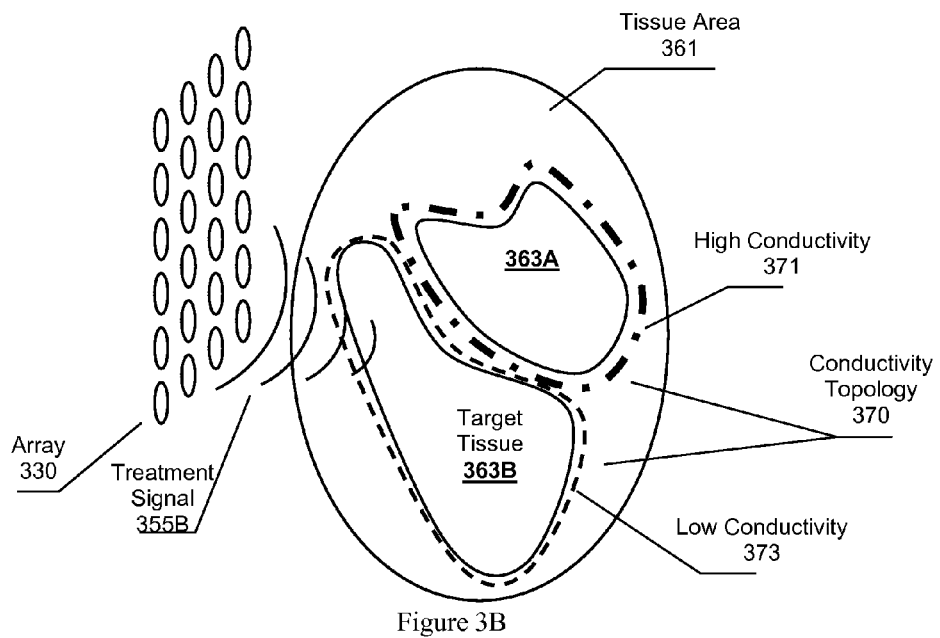
FIG. 3B illustrates targeting a tissue based on a measured conductivity topology where a target tissue lacks a significant contribution to the measured conductivity topology.

FIG. 3B provides another exemplary approach based on the same tissues of FIG. 3A. In this example, treatment signal 355B is constructed to target tissue 363B as opposed to tissue 363A. The measured low conductivity 373 of tissue 363B is considered lower than that of the measured conductivity 371 of tissue 363A. Rather than merely returning a high gain TRM acoustic signal back toward subject area 361, a TRM controller has constructed treatment signal 355A targeting a low signal area. Such an approach can be achieved by analyzing the measured conductivity topology of subject area 361 to derive values for various measured parameters. The measured parameters can be folded into one or more functions or algorithms used to generate treatment signal 355B, even if the selecting of parameters includes targeting areas lacking a significant contribution to the measured conductivity topology. For example, acoustic data from tissue 363A could be removed or filtered from the data set used to construct treatment signal 355A, possibly by filtering based on S/N.

The approach of selecting tissues based on the measured conductivity topology parameters can be used to target tissues that lack a significant contribution to the conductivity topology. For example, a feeder vessel to a tumor could be targeted as opposed to a tumor itself. Additionally, tissue surrounding a tumor could be targeted to isolate the tumor or isolate other tissues of interest.

Treatment signal 355A could also comprise a completely constructed TRM acoustic treatment signal. A TRM controller has a wealth of information regarding a measured conductivity topology based on the various measured parameters of the corresponding conductivity topology 370. The TRM controller can use the information, including other externally obtained information, to construct a calculated TRM acoustic treatment signal lacking a TRM component of an induced acoustic signal. For example, the TRM controller can use the measured geometry of the measured topology, electrical parameters, or other information to target tissues that lack a significant contribution to the measured parameters. One can consider this approach as targeting background regions (e.g., regions lacking significant signals), tissue 363B for example, as opposed to foreground regions (e.g., regions contributing significant signals). Alternatively one can consider the above approach as "inverting" the data similar to working with a photographic negative. Such an approach can be achieved by the TRM controller modeling a virtual acoustic signal based on the measured parameters where the virtual acoustic signal is model as if it originated from the background regions, tissue 363B for example. The virtual acoustic signal can then be used as foundation for generating the calculated TRM acoustic treatment signal as described above.

One should keep in mind that treatment signals 355A or 355B are emitted from array 330 comprising many individual, discrete transducers or other acoustic emitters. Each transducer is instructed individually to emit individual acoustic signals, which aggregate to form treatment signals 355A or 355B. The individual acoustic signals can be generated so that they constructively, or destructively, interfere properly at their respective target tissue. The constructed acoustic treatment signals can be formed by taking into account materials intermediary between array 330 and target tissues 363A or 363B. Intermediary materials could include other tissues having various acoustic transmission properties, density for example. A TRM controller can provide instructions to the individual transducers of array 330 to emit individual acoustic signal according to desired properties: frequency, amplitude, relative phase, location, timing, or other properties.

One should appreciate that a treatment can have temporal aspects where the treatment signals can vary with time under a controlled regime, possibly based on a programmed treatment. The TRM controller can adjust the treatment signal according the programmed treatment as desired, including in response to feedback from newly acquired acoustic data or from other external input (e.g., user input, MRI machine, etc.). As treatment is applied, the TRM controller can change the treatment signal(s) frequency, phase, chirping, amplitude, target location, or other properties.

One should appreciate that applying a treatment to a target tissue as discussed above is considered to include weighting an acoustic treatment signal based on measured parameters. For example, when applying a TRM acoustic treatment signal constructed based on the weighting of the S/N resulting from the conductivity topology, the resulting treatment is a conductivity weighted acoustic treatment. Still further, when the treatment signal has sufficient gain to ablate a target tissue, the TRM acoustic treatment signal represents a conductivity-weighted acoustic ablation signal. It is contemplated that any measured parameter could be used to weight the acoustic treatment signal.

Typically an input RF radiation comprises a single dominate frequency (f). When the radiation induces an acoustic signal, the acoustic signal has a dominate frequency component of 2f. It should be further appreciated that an input signal can include more than one component, possibly having more than one frequency peak, or even a spectrum.

Figure 4A:
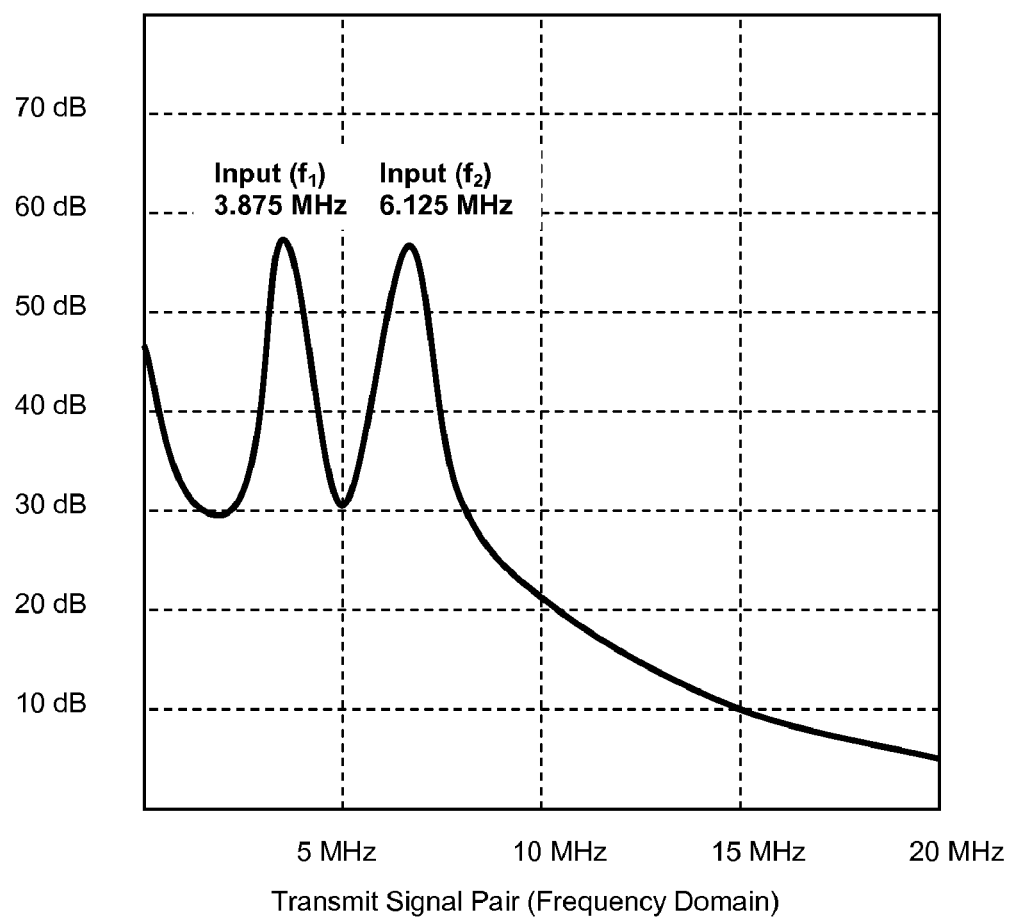
FIG. 4A presents an example pair of transmitted input RF signals.

Consider FIG. 4A where a pair of transmitted RF signals are generated at f1=3.875 MHz and f2=6.125 MHz and are directed to a target tissue. The graph is presented in the frequency domain to clearly illustrate there can be more than one frequency peak, or a spectrum. An expected acoustic signal (e.g., ultrasound) would have 2f components at 7.75 MHz and 12.25 MHz, two times the transmitted frequencies. Indeed that does occur. Interestingly, other acoustic peaks are also present that are distinct from the 2f components.

Figure 4B:
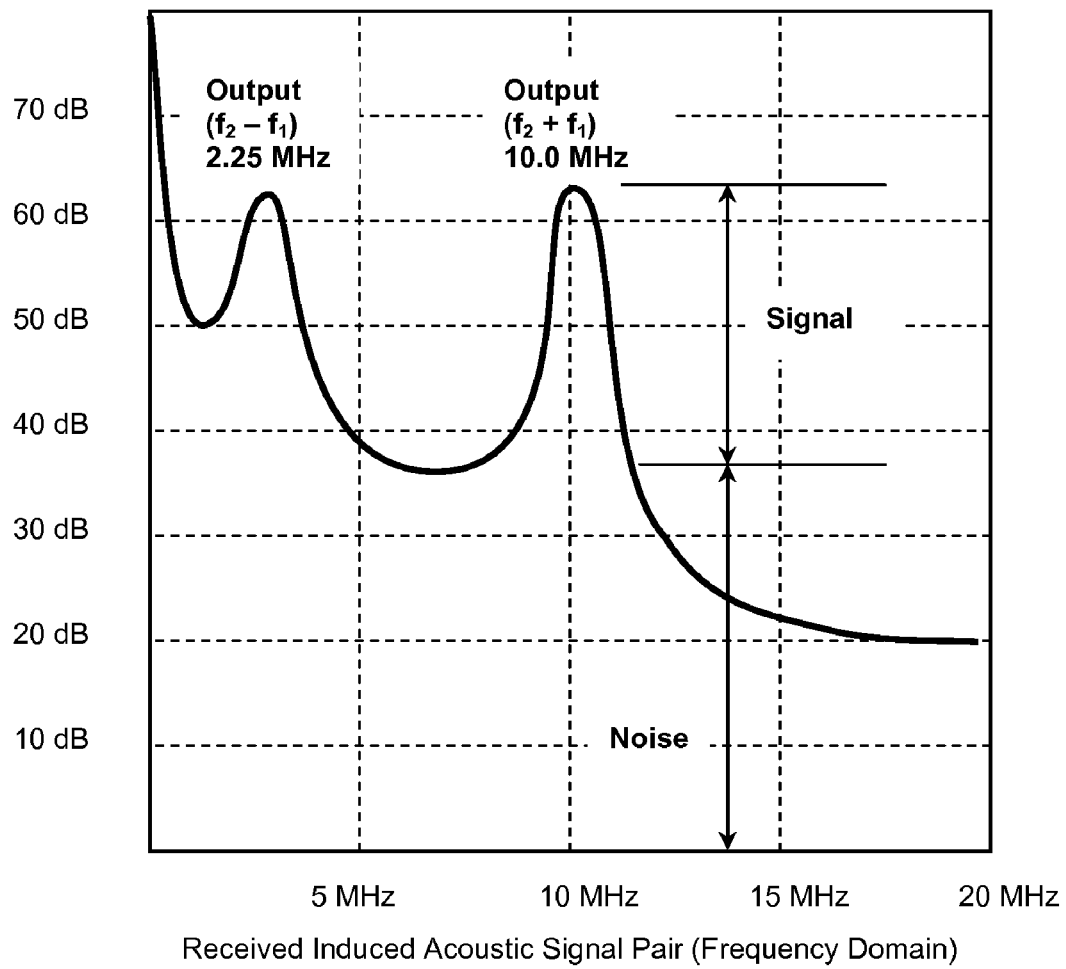
FIG. 4B presents received acoustic signals from the pair RF signal of FIG. 4A.

FIG. 4B illustrates received acoustic signals induced by the transmit pair of FIG. 4A. In this example, two main peaks are identified representing a difference between the pair's frequencies at f2−f1=2.25 MHz, and sum of the pair's frequency f2+f1=10 MHz. Note the 2f components are removed for clarity. Rather than filtering for just the 2f components as was previously done, the Applicants have recognized that other peaks, or parts of the frequency spectrum, carry additional information. For example, a first tissue might provide a strong difference component while a second tissue might provide a strong sum component. Therefore diagnostic or treatment information can be gained based on the recorded acoustic spectrum. Additional, TRM acoustic treatment signal can be constructed based on the other signals beyond the just the expect 2f components to selectively target the first or second tissue. Such information would have been lost using previously known techniques.

To generalize, a transmitted input RF signal can comprise multiple parts. When the input frequencies, or even spectra, are known, then the resulting induced acoustic signal can be used to characterize different tissues based on the inputs and the measured conductivity topologies. Once characterized, possibly based on S/N of the frequency peaks as illustrated, the properties of known tissues can be folded into construction of an appropriate TRM acoustic treatment.

Thus far the disclosed techniques have been presented within the context of providing a treatment, especially with respect to treating tumors through ablation or heating. Other types of treatments are also contemplated. One possible treatment includes targeting vein or artery maladies, possibly for cosmetic purposes, where varicose veins could be collapsed or spider veins could be eliminated. Another possible treatment could include lipoblasty where fatty tissues are targeted to reduce or eliminate fat. Yet another treatment can include reshaping corneas, correcting lens, or other ocular treatments.

It is further contemplated that a target tissue could be on the surface of a patient as opposed to being internal to a patient. A patient could be placed in an acoustic transmission medium (e.g., water, gel, etc.) and a TRM acoustic treatment signal can be constructed to pass through the medium to the surface tissue.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A time-reversal mirroring electromagnetic acoustic treatment system, the system, comprising:
   an electromagnetic signal source configured to emit electromagnetic radiation toward a subject tissue area having a conductivity gradient;
   an array of acoustic transducers configured to collect acoustic signals generated in response to the electromagnetic radiation inducing an induced acoustic signal from the subject tissue area;
   a TRM controller communicatively coupled to the array of acoustic transducers and configured to (a) collect acoustic data representative of the induced acoustic signal received by the array of acoustic transducers, (b) derive a measured conductivity topology of the subject tissue area by mapping signal to noise properties of the acoustic data to properties of the conductivity topology without requiring significant contribution from a target tissue within the subject tissue area, and (c) generate emitter instructions for a time-reversed acoustic signal from the acoustic data as a function of the measured conductivity topology, the time-reversed acoustic signal targeting a the target tissue; and
   an array of acoustic emitters coupled to the TRM controller and configured to emit the time-reversed acoustic signal according to the emitter instructions toward the target tissue.

2. The system of claim 1, wherein the time-reversed acoustic signal comprises sufficient gain to ablate a portion of the target tissue.

3. The system of claim 1, wherein the TRM controller is configured to generate the emitter instructions representative of the time-reversed acoustic signal for the target tissue as a function of measured parameters of the subject tissue area.

4. The system of claim 3, wherein the TRM controller is further configured to measure the subject tissue area measured parameters based on the acoustic data.

5. The system of claim 1, wherein the TRM controller is configured to identify the target tissue based on a threshold of the signal-to-noise ratio.

6. The system of claim 3, wherein the TRM controller is configured to measure the subject tissue area measured parameters based on reflections of emitted electromagnetic signals from the subject tissue area.

7. The system of claim 3, wherein the subject tissue area measured parameters are derived from at least one of the following: a sum of input transmitted RF frequencies, frequency chirp, and a difference of input transmitted RF frequencies.

8. The system of claim 1, further comprising a dual-mode imaging apparatus capable of simultaneously displaying an acoustic image derived from the acoustic data and an electromagnetic image derived from reflections of the emitted electromagnetic signals from the subject tissue area.

9. The system of claim 1, wherein the electromagnetic signal source comprises a magnetic resonance imaging system.

10. The system of claim 1, wherein the TRM controller is further configured to apply an ablative therapy to the target tissue in response to feedback received via the array of acoustic transducers.

11. The system of claim 1, wherein the induced acoustic signal comprises an induced ultrasound signal.

12. The system of claim 1, wherein the electromagnetic radiation comprises at least two EM signals having distinct frequency peaks.

13. The system of claim 1, wherein the measured conductivity topology comprises at least a three dimensional volume.

14. The system of claim 1, wherein the time-reversed acoustic signal comprises conductivity weighted treatment signal directed toward the target tissue.

15. A time-reversal mirroring electromagnetic acoustic treatment system, the system, comprising:
   an electromagnetic signal source configured to emit electromagnetic radiation toward a subject tissue area having a conductivity gradient;
   an array of acoustic transducers configured to collect acoustic signals generated in response to the electromagnetic radiation inducing an induced acoustic signal from the subject tissue area;
   a TRM passive controller communicatively coupled to the array of acoustic transducers and configured to (a) collect acoustic data representative of the induced acoustic signal received by the array of acoustic transducers, (b) derive a conductivity topology representing a three-dimensional model of a conductivity structure of the subject tissue area by mapping signal to noise properties of the acoustic data to properties of the conductivity topology without requiring significant contribution from a target tissue within the subject tissue area, and (c) generate emitter instructions for a time-reversed acoustic signal from the acoustic data based on the conductivity topology, the time-reversed acoustic signal targeting the target tissue; and
   an array of acoustic emitters coupled to the TRM controller and configured to emit the time-reversed acoustic signal according to the emitter instructions toward the target tissue.

* * * * *